United States Patent [19]

Himmele et al.

[11] Patent Number: 4,876,275

[45] Date of Patent: Oct. 24, 1989

[54] 3,4-DIHYDRO-2H-PYRANS USEFUL AS PESTICIDES

[75] Inventors: Walter Himmele, Walldorf; Hans Theobald, Limburgerhof; Franz Merger, Frankenthal; Ernst Hofmann, Ludwigshafen; Christoph Kuenast, Otterstadt; Peter Hofmeister, Neustadt, all of Fed. Rep. of Germany

[73] Assignee: BASF Aktiengesellschaft, Ludwigshafen, Fed. Rep. of Germany

[21] Appl. No.: 176,700

[22] Filed: Apr. 1, 1988

[30] Foreign Application Priority Data

Apr. 3, 1987 [DE] Fed. Rep. of Germany ....... 3711269

[51] Int. Cl.$^4$ .................... A01N 43/16; C07D 309/30
[52] U.S. Cl. ................................... 514/452; 514/460; 549/416; 549/415; 549/414; 549/378; 548/370; 548/341; 548/333; 548/331
[58] Field of Search ............... 549/416, 414, 415, 370, 549/378, 341, 333, 331; 514/452, 460

[56] References Cited

U.S. PATENT DOCUMENTS 3,691,205 9/1972 Hoffmann et al. ................. 549/416

FOREIGN PATENT DOCUMENTS

WO84/02910 8/1984 PCT Int'l Appl. .
2104061 3/1983 United Kingdom .

OTHER PUBLICATIONS

Chemical Reviews, 75, 651–692 (1975).
Chemical Abstracts, 69, 67171z (1968).
Chemical Abstracts, 73, 98731u (1970).
Chemical Abstracts, 76, 14250n (1972).
Chemical Abstracts, 81, 3720t (1974).
Chemical Abstracts, 93, 25857t (1980).
Chemical Abstracts, 101, 23272h (1984).
Khim. Geterotsikl. Soedin., 6, 730 (1970).

Primary Examiner—Nicky Chan
Attorney, Agent, or Firm—Keil & Weinkauf

[57] ABSTRACT 3,4-dihydro-2H-pyrans of the formula I

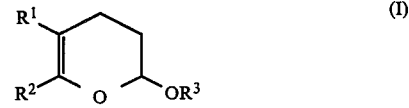

where $R^1$ is $C_4$–$C_{20}$-alkyl, $C_4$–$C_{20}$-alkoxyalkyl, aryl or $C_7$–$C_{20}$-arylalkyl, or is aryl or $C_7$–$C_{20}$-arylalkyl which bears from one to three substituents selected from the group consisting of halogen, $C_1$–$C_8$-alkyl, $C_1$–$C_8$-haloalkyl, $C_1$–$C_8$-alkoxy or $C_1$–$C_8$-haloalkoxy, $R^2$ is hydrogen or $C_1$–$C_4$-alkyl, $R^3$ is aryl, or aryl bearing from one to three substituents selected from the group consisting of halogen, $C_1$–$C_8$-alkyl, $C_1$–$C_8$-haloalkyl, $C_1$–$C_8$-alkoxy or $C_1$–$C_8$-haloalkoxy, or the radical

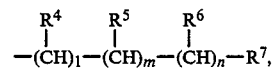

where $R^4$, $R^5$ and $R^6$ are hydrogen or $C_1$–$C_4$-alkyl, $R^7$ is phenyl or benzoyl, or phenyl or benzoyl bearing from one to three substituents selected from the group consisting of halogen, $C_1$–$C_8$-alkyl, $C_1$–$C_8$-haloalkyl, $C_1$–$C_8$-alkoxy and $C_1$–$C_8$-haloalkoxy, or a five- or six-membered heterocycle containing one or two oxygen atoms and which is either unsubstituted or substituted by one to three $C_1$–$C_8$-alkyl groups or one $C_3$–$C_6$-spirocycloalkyl, and l, m and n are 0 or 1, and their use for combating pests.

6 Claims, No Drawings

3,4-DIHYDRO-2H-PYRANS USEFUL AS PESTICIDES

The present invention relates to novel 3,4-dihydro-2H-pyrans of the general formula I

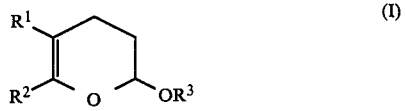

where $R^1$ is $C_4$–$C_{20}$-alkyl or $C_4$–$C_{20}$-alkoxyalkyl or is aryl or $C_7$–$C_{20}$-aralkyl, each of which is monosubstituted to trisubstituted by halogen, $C_1$–$C_8$-alkyl, $C_1$–$C_8$-haloalkyl, $C_1$–$C_8$-alkoxy or $C_1$–$C_8$-haloalkoxy, $R^2$ is hydrogen or $C_1$–$C_4$-alkyl, $R^3$ is alkyl or is aryl which is monosubstituted to trisubstituted by halogen, $C_1$–$C_8$-alkyl, $C_1$–$C_8$-haloalkyl, $C_1$–$C_8$-alkoxy or $C_1$–$C_8$-haloalkyl, or is a radical

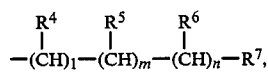

where $R^4$, $R^5$ and $R^6$ are each hydrogen or $C_1$–$C_4$-alkyl, $R^7$ is phenyl or benzoyl, each of which is unsubstituted or monosubstituted to trisubstituted by halogen, $C_1$–$C_8$-alkyl, $C_1$–$C_8$-haloalkyl, $C_1$–$C_8$-alkoxy or $C_1$–$C_8$-haloalkoxy, or a 5-membered or 6-membered heterocyclic which contains one or two oxygen atoms and is unsubstituted or substituted by one to three $C_1$–$C_8$-alkyl groups or a $C_3$–$C_6$-spirocycloalkyl group, and l, m and n are each zero or 1.

The present invention furthermore relates to the preparation of the compounds I, pesticides which contain the compounds I is active ingredients and a method for controlling pests.

Chemical Reviews 75 (1975), 651–692; Chemical Abstracts 69, 67171z; 73, 98731u; 76, 14250n; 81, 3720t; 93, 25857t and 101, 23272h; and Khim. Geterotsikl. Soedin. 6 (1970), 730 and U.S. Pat. No. 3,691,205 disclose compounds which are structurally similar but are not described as active ingredients for pesticides.

It is an object of the present invention to provide novel 3,4-dihydro-2H-pyrans I.

We have found that this object is achieved by the novel 3,4-dihydro-2H-pyrans I defined at the beginning and processes for their preparation. Surprisingly, the novel compounds I are suitable as pesticides.

The compounds I are obtainable by the following methods:

(a) by reacting a vinyl ether II with a monomeric α,β-unsaturated aldehyde or ketone III according to the following equation:

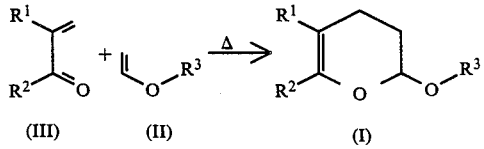

or (b) by reacting a vinyl ether II with a dimeric α,β-unsaturated aldehyde or ketone IIIa

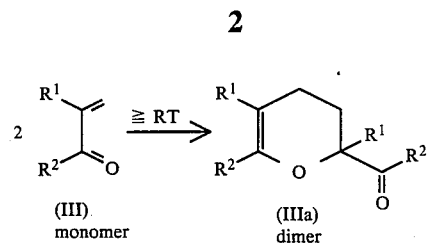

according to the following equation

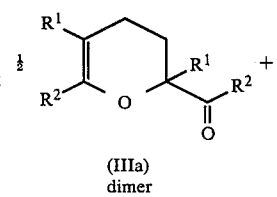

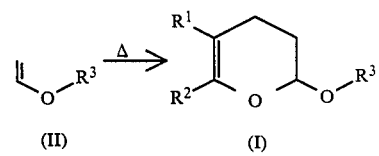

In both cases, the reaction is carried out in the same way. The reactions (a) and (b) are carried out in the presence of a free radical inhibitor and a basic compound at from 130° to 280° C., preferably from 160° to 220° C., particularly preferably from 180° to 210° C., under from 1 to 300 bar. These reactions are preferably carried out under a protective gas atmosphere. Examples of suitable protective gases are nitrogen and argon. If the educt components permit (appropriately high boiling point), the reactions can be carried out under atmospheric pressure (about 1 bar). In all other cases, it is advisable to carry out the reaction in an autoclave under autogenous pressure of from >1 to 300 bar. The reaction temperature can of course be reduced by prepressurizing the autoclave. The sum of the selected prepressure and the autogenous pressure which additionally builds up during heating remains in the range of up to 300 bar.

Suitable free radical inhibitors are polymerization inhibitors known from the prior art, such as phenols, in particular substituted phenols, eg. cresols, 2,6-ditert-butyl-4-methylphenol and preferably hydroquinone, or hydroquinone monoalkyl ethers, such as hydroquinone monomethyl ether. Hydroquinone is particularly preferred.

Examples of suitable basic compounds are alkali metal and alkaline earth metal carbonates or bicarbonates, in particular sodium carbonate, potassium carbonate and calcium carbonate, sodium carbonate being preferred. The basic compounds are used for binding any traces of acid, in order to avoid decomposition of the vinyl ethers by the action of acid. Acid may be formed, for example, by cleavage reactions or oxidation, in particular in the presence of air or where impure starting materials are used. The amount of base is not particularly critical; if pure starting materials are used and the reaction is carried out in an inert gas atmospheric, catalytic amounts, eg. from 0.01 to 0.05 mole per mole of vinyl ether, are sufficient.

In general, the reaction is carried out in the absence of a solvent or diluent, but may also be effected in a solvent or diluent. Examples of suitable substances for this purpose are aromatic hydrocarbons, such as benzene, toluene or xylene, or ethers, such as diphenyl ether. Mixtures of these substances may also be used as solvents or diluents.

To prepare the novel compounds I by the methods described above, the starting materials II and III are used in a molar ratio of from 0.8:1 to 5:1, preferably from 0.9:1 to 2.5:1, particularly preferably from 1:1 to 1.5:1. The same also applies to the dimeric compounds IIIa.

The compounds II are known per se or can be prepared by a conventional method (Annalen der. Chemie, 601 (1956), 81–138).

The compounds III and IIIa are likewise known per se or can be prepared by a conventional method (Houben-Weyl, Methoden der organischen Chemie, Vol. VII/2b, 4th edition, 1976, pages 1457 et seq and 1482 et seq).

The reaction of II with III to give I can also be catalyzed with a Lewis acid (DE-A-21 63 515).

The substituents have the following specific meanings:

$R^1$ is $C_4$–$C_{20}$-alkyl, preferably $C_4$–$C_{12}$-alkyl, particularly preferably $C_4$–$C_8$-alkyl, such as n-butyl, isobutyl, sec-butyl, tert-butyl, n-pentyl, isopentyl, n-hexyl, isohexyl, n-octyl, 1,3,3-trimethylbutyl or 2,4,4-trimethylbutyl, $C_4$–$C_{20}$-alkoxyalkyl, preferably $C_4$–$C_{12}$-alkoxyalkyl, particularly preferably $C_4$–$C_8$-alkoxyalkyl, such as methoxy-n-propyl, methoxyisopropyl, n-propoxymethyl, isopropoxymethyl, 2-ethoxyethyl, tert-butoxymethyl, 2-(tert-butoxy)-ethyl, 2-(tert-butoxy)-n-propyl or 2-(tert-butoxy)-isopropyl, aryl, such as phenyl and naphthyl, preferably phenyl, $C_7$–$C_{20}$-aralkyl, preferably $C_7$–$C_{12}$-aralkyl, particularly preferably $C_7$–$C_{10}$-aralkyl, such as benzyl, 1-phenylethyl, 2-phenylethyl, 1-phenyl-n-propyl, 2-phenyl-n-propyl, 2-phenylisopropyl or 3-phenyl-n-propyl, aryl which is monosubstituted to trisubstituted by halogen, preferably phenyl which is monosubstituted or disubstituted by fluorine or chlorine, particularly preferably phenyl which is monosubstituted by fluorine or chlorine, such as 4-fluorophenyl or 4-chlorophenyl, aryl which is monosubstituted to trisubstituted by $C_1$–$C_8$-alkyl, preferably phenyl which is monosubstituted or disubstituted by $C_1$–$C_4$-alkyl, particularly preferably phenyl which is monosubstituted by $C_1$- or $C_2$-alkyl, such as 4-methylphenyl or 4-ethylphenyl, aryl which is monosubstituted to trisubstituted by $C_1$–$C_8$-haloalkyl, preferably phenyl which is monosubstituted or disubstituted by $C_1$–$C_4$-fluoro- or chloroalkyl, particularly preferably phenyl which is substituted by $C_1$- or $C_2$-fluoro- or -chloroalkyl, such as 4-trifluoromethylphenyl or 4-trichloromethylphenyl, aryl which is monosubstituted to trisubstituted by $C_1$–$C_8$-alkoxy, preferably phenyl which is monosubstituted or disubstituted by $C_1$–$C_4$-alkoxy, particularly preferably phenyl which is monosubstituted by $C_1$- or $C_2$-alkoxy, such as 4-methoxyphenyl or 4-ethoxyphenyl, aryl which is monosubstituted to trisubstituted by $C_1$–$C_8$-haloalkoxy, preferably phenyl which is monosubstituted or disubstituted by $C_1$–$C_4$-fluoro- or chloroalkoxy, particularly preferably phenyl which is monosubstituted by $C_1$–$C_2$-fluoro- or chloroalkoxy, such as 4-(trifluoromethoxy)phenyl or 4-(trichloromethoxy)phenyl, $C_7$–$C_{20}$-aralkyl which is monosubstituted to trisubstituted by halogen, preferably benzyl which is monosubstituted or disubstituted by fluorine or chlorine, particularly preferably benzyl which is monosubstituted by fluorine or chlorine, such as 4-fluorobenzyl or 4-chlorobenzyl, $C_7$–$C_{20}$-aralkyl which is monosubstituted to trisubstituted by $C_1$–$C_8$-alkyl, preferably benzyl which is monosubstituted or disubstituted by $C_1$–$C_4$-alkyl, particularly preferably benzyl which is monosubstituted by $C_1$- or $C_2$-alkyl, such as 4-methylbenzyl or 4-ethylbenzyl, $C_7$–$C_{20}$-aralkyl which is monosubstituted to trisubstituted by $C_1$–$C_8$-haloalkyl, preferably benzyl which is monosubstituted or disubstituted by $C_1$–$C_4$-fluoro- or chloroalkyl, particularly preferably benzyl which is substituted by $C_1$- or $C_2$-fluoro- or -chloroalkyl, such as 4-trifluoromethylbenzyl or 4-trichloromethylbenzyl, $C_7$–$C_{20}$-aralkyl which is monosubstituted to trisubstituted by $C_1$–$C_8$-alkoxy, preferably benzyl which is monosubstituted or disubstituted by $C_1$–$C_4$-alkoxy, particularly preferably benzyl which is monosubstituted by $C_1$- or $C_2$-alkoxy, such as 4-methoxybenzyl or 4-ethoxybenzyl, $C_7$–$C_{20}$-aralkyl which is monosubstituted to trisubstituted by $C_1$–$C_8$-haloalkoxy, preferably benzyl which is monosubstituted or disubstituted by $C_1$–$C_4$-fluoro- or chloroalkoxy, particularly preferably benzyl which is monosubstituted by $C_1$- or $C_2$-fluoro- or chloroalkoxy, such as 4-(trifluoromethoxy)benzyl or 4-(trichloromthoxy)benzyl, the aryl and aralkyl radicals preferably being phenyl or phenylalkyl radicals, $R^2$ is hydrogen, $C_1$–$C_4$-alkyl, preferably $C_1$- or $C_2$-alkyl, particularly preferably methyl, $R^3$ is aryl, such as phenyl or naphthyl, preferably phenyl, aryl which is monosubstituted to trisubstituted by halogen, preferably phenyl which is monosubstituted or disubstituted by fluorine or chlorine, particularly preferably phenyl which is monosubstituted by fluorine or chlorine, such as 2-fluorophenyl, 4-fluorophenyl, 2-chlorophenyl or 4-chlorophenyl, aryl which is monosubstituted to trisubstituted by $C_1$–$C_8$-alkyl, preferably phenyl which is monosubstituted or disubstituted by $C_1$–$C_4$-alkyl, particularly preferably phenyl which is monosubstituted by $C_1$–$C_4$-alkyl, such as 4-methylphenyl, 4-ethylphenyl, 4-isopropylphenyl, 4-sec-butylphenyl or 4-tert-butylphenyl, aryl which is monosubstituted to trisubstituted by $C_1$–$C_8$-haloalkyl, preferably phenyl which is monosubstituted or disubstituted by $C_1$–$C_4$-fluoro- or chloroalkyl, particularly preferably phenyl which is substituted by $C_1$- or $C_2$-fluoro or -chloroalkyl, such as 4-trifluoromethylphenyl or 4-trichloromethylphenyl, aryl which is monosubstituted to trisubstituted by $C_1$–$C_8$-alkoxy, preferably phenyl which is monosubstituted or disubstituted by $C_1$–$C_4$-alkoxy, particularly preferably phenyl which is monosubstituted by $C_1$- or $C_2$-alkoxy, such as 4-methoxyphenyl or 4-ethoxyphenyl, aryl which is monosubstituted to trisubstituted by $C_1$–$C_8$-haloalkoxy, preferably phenyl which is monosubstituted or disubstituted by $C_1$–$C_4$-fluoro- or chloroalkoxy, particularly preferably phenyl which is monosubstituted by $C_1$- or $C_2$-fluoro- or chloroalkoxy, such as 4-trifluoromethoxy)phenyl or 4-(trichloromethoxy)phenyl, aryl which is disubstituted or trisubstituted by both halogen and $C_1$–$C_8$-alkyl, preferably phenyl which is disubstituted by fluorine or chlorine and $C_1$–$C_4$-alkyl, such as 3-methyl-4-chlorophenyl, the aryl radicals preferably being phenyl radicals,

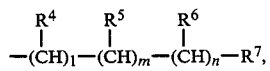

$R^4$, $R^5$ and $R^6$ are each hydrogen, $C_1$–$C_4$-alkyl, preferably $C_1$ or $C_2$-alkyl, particularly preferably methyl, and $R^7$ is phenyl, benzoyl, phenyl which is monosubstituted to trisubstituted by halogen, preferably phenyl which is monosubstituted or disubstituted by fluorine or chlorine, particularly preferably phenyl which is monosubstituted by fluorine or chlorine, such as 4-fluorophenyl or 4-chlorophenyl, phenyl which is monosubstituted to trisubstituted by $C_1$–$C_8$-alkyl, preferably phenyl which is monosubstituted or disubstituted by $C_1$–$C_4$-alkyl, particularly preferably phenyl which is monosubstituted by $C_1$- or $C_2$-alkyl, such as 4-methylphenyl or 4-ethylphenyl, phenyl which is monosubstituted to trisubstituted by $C_1$–$C_8$-haloalkyl, preferably phenyl which is monosubstituted or disubstituted by $C_1$–$C_4$-fluoro- or chloroalkyl, particularly preferably phenyl which is substituted by $C_1$- or $C_2$-fluoro- or -chloroalkyl, such as 4-trifluoromethylphenyl or 4-trichloromethylphenyl, phenyl which is monosubstituted to trisubstituted by $C_1$–$C_8$-alkoxy, preferably phenyl which is monosubstituted or disubstituted by $C_1$–$C_4$-alkoxy, particularly preferably phenyl which is monosubstituted by $C_1$- or $C_2$-alkoxy, such as 4-methoxyphenyl or 4-ethoxyphenyl, phenyl which is monosubstituted to trisubstituted by $C_1$–$C_8$-haloalkoxy, preferably phenyl which is monosubstituted or disubstituted by $C_1$–$C_4$-fluoro- or chloroalkoxy, particularly preferably phenyl which is monosubstituted by $C_1$- or $C_2$-fluoro- or chloroalkoxy, such as 4-(trifluoromethoxy)phenyl or 4-(trichloromethoxy)phenyl, benzoyl which is monosubstituted to trisubstituted by halogen, preferably benzoyl which is monosubstituted or disubstituted by fluorine or chlorine, particularly preferably benzoyl which is monosubstituted by fluorine or chlorine, such as 4-fluorobenzoyl or 4-chlorobenzoyl, benzoyl which is monosubstituted to trisubstituted by $C_1$–$C_8$-alkyl, preferably benzoyl which is monosubstituted or disubstituted by $C_1$–$C_4$-alkyl, particularly preferably benzoyl which is monosubstituted by $C_1$- or $C_2$-alkyl, such as 4-methylbenzoyl or 4-ethylbenzoyl, benzoyl which is monosubstituted to trisubstituted by $C_1$–$C_8$-haloalkyl, preferably benzoyl which is monosubstituted or disubstituted by $C_1$–$C_4$-fluoro- or chloroalkyl, particularly preferably benzoyl which is substituted by $C_1$- or $C_2$-fluoro- or -chloroalkyl, such as 4-trifluoromethylbenzoyl and 4-trichloromethylbenzoyl, benzoyl which is monosubstituted to trisubstituted by $C_1$–$C_8$-alkoxy, preferably benzoyl which is monosubstituted or disubstituted by $C_1$–$C_4$-alkoxy, particularly preferably benzoyl which is monosubstituted by $C_1$- or $C_2$-alkoxy, such as 4-methoxybenzoyl or 4-ethoxybenzoyl, benzoyl which is monosubstituted to trisubstituted by $C_1$–$C_8$-haloalkoxy, preferably benzoyl which is monosubstituted or disubstituted by $C_1$–$C_4$-fluoro- or chloroalkoxy, particularly preferably benzoyl which is monosubstituted by $C_1$- or $C_2$-fluoro- or chloroalkoxy, such as 4-(trifluoromethoxy)benzoyl or 4-(trichloromethoxy)benzoyl, a 5-membered or 6-membered heterocyclic containing one or two oxygen atoms, preferably furan-2-1-yl, tetrahydrofuran-2-yl, 2H-pyran-2-yl, 4H-pyran-2-yl, 3,4-dihydro-2H-pyran-2-yl or tetrahydropyran, particularly preferably 2,5-dioxan-1-yl, 3,5-dioxan-1-yl, 3,6-dioxan-1-yl or 2,4-dioxolan-1-yl.

The 3,4-dihydro-2H-pyrans of the general formula I are suitable for effectively controlling pests from the class consisting of insects, arachnids and nematodes. They can be used as pesticides in crop protection and in the hygiene, material protection and veterinary sectors.

In contrast to most of the active ingredients known to date, which kill, incapacitate or repel the animals by acting as contact or ingested poisons, most of the compounds of the formula I intervene in the hormonal system of the animal organism. In the case of insects, for example, the transformation to the imago, the laying of viable eggs and the development of normal laid eggs are disturbed and hence the sequence of generations interrupted. The novel active ingredients are virtually completely non-toxic for vertebrates. Most of the compounds of the formula I are moreover readily degraded to form substances which occur in nature and are further decomposed by microorganisms.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani,*

*Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica* 12-*punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coacrtata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples of nematodes are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methyl-pyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 37 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 58 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 20 parts by weight of compound no. 61 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are 0.0001 to 10, and preferably from 0.01 to 1, %. The active ingredients may also successfully be used in the ultra-low-volume (ULV) method, where it is possible to apply formulations containing more than 95 wt% of active ingredient, or even the active ingredient without additives.

In the open, the amount of active ingredient applied is for example from 0.02 to 10, and preferably from 0.08 to 0.8, kg/ha.

There may be added to the active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O-O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl- 4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-ylmethyl)-phosphorodithioate, O,O-dimethyl-S-[4,6-diamino-1,3,5-triazin-2-yl)-methyl]-phosphorodithioate, O,O-diethyl-(1- phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

MANUFACTURING EXAMPLES

Example 1

5-benzyl-2-(p-chlorophenoxy)-3,4-dihydro-2H-pyran (compound 1)

49 g of 2-benzylacrolein, 70 g of p-chlorophenylvinyl ether, 1 g of hydroquinone and 0.5 g of sodium carbonate are stirred for 24 hours under a nitrogen blanket. Subsequent fractional distillation gives 78 g of 5-benzyl-2-(p-chlorophenoxy)-3,4-dihydro-2H-pyran (compound 1); yield: 75%, purity: 98%; b.p. (2 mbar) 185°–200° C.

Example 2

5-(1,3,3-trimethylbutyl)-2-(p-fluorophenoxy)-3,4-dihydro-2H-pyran (compound 2)

In an autoclave purged with nitrogen, 39 g of 2-methylene-3,5,5-trimethylhexan-1-ol, 35 g of p-fluorophenylvinyl ether, 0.5 g of hydroquinone and 0.5 g of sodium carbonate are stirred for 24 hours at autogenous pressure at 200° C. and the mixture is worked up in conventional manner. There is obtained 31 g of 5-(1,3,3-trimethylbutyl)-2-(p-fluorophenoxy)-3,4-dihydro-2H-pyran (compound 2); yield: 43%, purity: 94%; b.p. (2 mbar) 130°–136° C.

Example 3

6-methyl-5-phenyl-2-(p-fluorophenoxy)-3,4-dihydro-2H-pyran (compound 3)

In an autoclave purged with nitrogen, 29 g of 6-methyl-5-phenyl-2-acetyl-2-phenyl-3,4-dihydro-2H-pyran, 34.5 g of p-fluorophenylvinyl ether, 0.5 g of hydroquinone and 0.5 g of sodium carbonate are stirred for 24 hours at 190° C. at autogenous pressure and the mixture is worked up in conventional manner. There is obtained 29.5 g of 6-methyl-5-phenyl-2-(p-fluorophenoxy)-3,4-dihydro-2H-pyran (compound 3) in a yield of 90%, based on the pyran derivative, and a purity of 98.5%; b.p. (2 mbar) 127°–130° C.

Compounds I in Tables 1 and 2 below were also obtained by the routes described in Examples 1 to 3.

TABLE 1

(I)

| Compound No. | $R^1$ | $R^2$ | $R^3$ | bp. [°C.]/mbar | mp [°C.] |
|---|---|---|---|---|---|
| 4 | benzyl | H | 2-fluorophenyl | 152–160/2 | |
| 5 | 1-phenylethyl | H | 4-chlorophenyl | 190–200/2 | |
| 6 | 1-phenylethyl | H | 4-methylphenyl | 176–186/2 | |
| 7 | 1,3,3-trimethylbutyl | H | 4-chlorophenyl | 168–174/2 | |
| 8 | 1,3,3-trimethylbutyl | H | 4-methylphenyl | 157–166/2 | |
| 9 | phenyl | $CH_3$ | 4-chlorophenyl | 170–172/2 | |
| 10 | phenyl | $CH_3$ | 4-methylphenyl | 160–168/2 | |
| 11 | 2-tert.-butyloxypropyl | H | 4-chlorophenyl | 145–147/2 | |
| 12 | 2-tert.-butyloxypropyl | H | 4-fluorophenyl | 140–147/2 | |
| 13 | 2-tert.-butyloxypropyl | H | 4-methylphenyl | 140/2 | |
| 14 | n-hexyl | H | 4-chlorophenyl | 165–170/2 | |
| 15 | benzyl | H | 4-methylphenyl | 178–190/2 | |
| 16 | benzyl | H | 4-ethylphenyl | 195–205/4 | |
| 17 | benzyl | H | 2,4-dichlorophenyl | 190–200/1 | |
| 18 | benzyl | H | 3-chlorophenyl | 180–185/2 | |
| 19 | benzyl | H | 3,5-dimethyl-4-chlorophenyl | 195–205/2 | |
| 20 | benzyl | H | 4-methoxyphenyl | 185–187/2 | |
| 21 | benzyl | H | 3-methyl-4-chlorophenyl | 186–190/2 | |
| 22 | benzyl | H | 4-tert.-butylphenyl | | 83–85 |
| 23 | benzyl | H | 4-fluorophenyl | 160–175/2 | |
| 24 | benzyl | H | phenyl | 160–170/2 | |
| 25 | benzyl | H | 2-chlorophenyl | 180–185/2 | |
| 26 | 1-phenylethyl | H | 4-tert.-butylphenyl | 190–200/2 | |
| 27 | 1-phenylethyl | H | 4-fluorophenyl | 160–170/2 | |
| 28 | 1-phenylethyl | H | phenyl | 162–170/2 | |
| 29 | 1,3,3-trimethylbutyl | H | 4-methoxyphenyl | 173–175/2 | |
| 30 | 1,3,3-trimethylbutyl | H | phenyl | 126/2 | |
| 31 | 2-tert.-butyloxyethyl | H | 4-methylphenyl | 140–142/2 | |
| 32 | 2-tert.-butyloxyethyl | H | 4-chlorophenyl | 140–142/3 | |
| 33 | 2-tert.-butyloxyethyl | H | 4-fluorophenyl | 135/2 | |
| 34 | 2,4,4-trimethylbutyl | H | 4-tert.-butylphenyl | 158–164/2 | |

TABLE 2

$$R^1\underset{R^2}{\diagdown}{=}\diagup\underset{O}{\diagdown}\diagup\diagdown_{O-(CH_2)_l-(CH_2)_m-R^7} \quad (Ia)$$

| Compound No. | R¹ | R² | R⁷ | l | m | bp. [°C.]/mbar |
|---|---|---|---|---|---|---|
| 35 | benzyl | H | 1-ethyl-4-methyl-3,5-dioxan-1-yl | 1 | 0 | 162–165/2 |
| 36 | benzyl | H | 3-methyl-2,4-dioxolan-1-yl | 1 | 0 | 160–168/2 |
| 37 | benzyl | H | 3-methyl-2,4-dioxolan-1-yl | 1 | 1 | 180–186/2 |
| 38 | benzyl | H | 3,3-dimethyl-2,4-dioxolan-1-yl | 1 | 0 | 137–140/2 |
| 39 | benzyl | H | 1,3-dimethyl-2,4-dioxolan-1-yl | 1 | 0 | 131–132/2 |
| 40 | benzyl | H | 3,3-diethyl-2,4-dioxolan-1-yl | 1 | 0 | 160–162/2 |
| 41 | benzyl | H | 3,3-spirocyclo-pentyl-2,4-dioxolan-1-yl | 1 | 0 | 177–180/2 |
| 42 | benzyl | H | 3,3-Spirocyclo-hexyl-2,4-dioxolan-1-yl | 1 | 0 | 173–178/2 |
| 43 | 1-phenylethyl | H | 3-methyl-2,4-dioxolan-1-yl | 1 | 0 | 175–180/2 |
| 44 | 1-phenylethyl | H | 3,3-dimethyl-2,4-dioxolan-1-yl | 1 | 0 | 190/2 |
| 45 | 1-phenylethyl | H | 3-benzyl-2,4-dioxolan-1-yl | 1 | 0 | 216–226/2 |
| 46 | 1-phenylethyl | H | 3-methyl-3-(4-chlorophenyl)-2,4-dioxolan-1-yl | 1 | 0 | 210–226/2 |
| 47 | 1,3,3-trimethylbutyl | H | 3-methyl-2,4-dioxolan-1-yl | 1 | 1 | 140–145/2 |
| 48 | 1,3,3-trimethylbutyl | H | 3,3-dimethyl-2,4-dioxolan-1-yl | 1 | 0 | 135–140/2 |
| 49 | 1,3,3-trimethylbutyl | H | 3-benzyl-2,4-dioxolan-1-yl | 1 | 0 | 186–198/2 |
| 50 | 1,3,3-trimethylbutyl | H | 3-methyl-3-(4-chlorophenyl)-2,4-dioxolan-1-yl | 1 | 0 | 200–210/2 |
| 51 | 1,3,3-trimethylbutyl | H | 3,3-spirocyclopentyl-2,4-dioxolan-1-yl | 1 | 0 | 146–150/2 |
| 52 | 1,3,3-trimethylbutyl | H | 3,3-diethyl-2,4-dioxolan-1-yl | 1 | 0 | 140–150/2 |
| 53 | 1,3,3-trimethylbutyl | H | 3-methyl-2,4-dioxolan-1-yl | 1 | 0 | 120–124/2 |
| 54 | phenyl | CH₃ | 3-methyl-2,4-dioxolan-1-yl | 1 | 0 | 147/2 |
| 55 | phenyl | CH₃ | 3-methyl-2,4-dioxolan-1-yl | 1 | 1 | 148–149/2 |
| 56 | phenyl | CH₃ | 3,3-dimethyl-2,4-dioxolan-1-yl | 1 | 0 | 148/2 |
| 57 | n-butyl | H | 3-methyl-2,4-dioxolan-1-yl | 1 | 0 | 146–150/2 |
| 58 | 2-tert.-butyloxyethyl | H | 3-methyl-2,4-dioxolan-1-yl | 1 | 0 | 128–132/2 |
| 59 | 2-tert.-butyloxyethyl | H | 3,3-dimethyl-2,4-dioxolan-1-yl | 1 | 0 | 132–133/2 |
| 60 | 2-tert.-butyloxyethyl | H | 3-methyl-2,4-dioxolan-1-yl | 1 | 1 | 126–130/2 |
| 61 | 2-methyl-2-tert.-butyloxy-ethyl | H | 3-methyl-2,4-dioxolan-1-yl | 1 | 0 | 145–156/4 |
| 62 | 2-tert.-butyloxy-propyl | H | 3,3-dimethyl-2,4-dioxolan-1-yl | 1 | 0 | 133/2 |
| 63 | 2-tert.-butyloxy-propyl | H | 3-methyl-2,4-dioxolan-1-yl | 1 | 1 | 140–143/3 |
| 64 | 1,3,3-trimethylbutyl | H | 1-ethyl-4-methyl-4-phenyl-3,5-dioxan-1-yl | 1 | 0 | 200–210/2 |
| 65 | 1,3,3-trimethylbutyl | H | 3-methyl-2,4-dioxolan-1-yl | 1 | 0 | 120–126/2 |
| 66 | 1,3,3-trimethylbutyl | H | 3-isopropyl-2,4-dioxolan-1-yl | 1 | 0 | 135–146/2 |
| 67 | 1,3,3-trimethylbutyl | H | 3-isobutyl-2,4-dioxolan-1-yl | 1 | 0 | 180/4 |
| 68 | 1,3,3-trimethylbutyl | H | 3-methyl-3-ethyl-2,4-dioxolan-1-yl | 1 | 0 | 122–124/2 |
| 69 | 1,3,3-trimethylbutyl | H | 3-tert.-butyl-2,4-dioxolan-1-yl | 1 | 0 | 145–146/1 |
| 70 | 1,3,3-trimethylbutyl | H | 2,4-dimethyl-3,6-dioxan-1-yl | 1 | 0 | 112–115/2 |
| 71 | 1,3,3-trimethylbutyl | H | 4-isopropyl-3,5-dioxan-1-yl | 1 | 0 | 120–125/2 |
| 72 | 1,3,3-trimethylbutyl | H | 3-(2,4,4-trimethylpentyl)-2,4-dioxolan-1-yl | 1 | 0 | 180–187/1 |
| 73 | 1,3,3,-trimethylbutyl | H | 3-methyl-2,5-dioxan-1-yl | 1 | 1 | 155/3 |

USE EXAMPLES

Example A

Breeding experiment with Dysdercus intermedius (cotton stainer)

1 ml of acetonic solutions of the active ingredients were used to line Petri dishes 10 cm in diameter. After the solvent had evaporated, 20 larvae of the penultimate stage were placed in the dishes. After 24 hours the survivors were transferred to 1 liter jars containing 200 g of sterile quartz sand (particle size: 0 to 3 mm). This sand had been watered prior to the experiment with 25 ml of aqueous formulations of the active ingredients. The food proffered was swollen cotton seeds which were replaced once a week. The sand was also moistened once a week with pure water.

The temperature was kept at 25° to 27° C. The jars were monitored until the the eggs in the control jars hatched. The following factors were assessed:
1. morality (weekly)
2. molting to adult and registration of any deformations
3. egg deposition
4. hatching In this experiment, the lethal dose of compounds 1, 2, 7, 32, 33, 36, 54, 58, 61 and 63 was either 1.0 ppm or less. Generally, the lethal dose was from 0.4 to 0.2 ppm, and-in exceptional cases-0.004 ppm.

Example 2

Ovicidal action on Dysdercus intermedius (cotton stainer)

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel. The eggs were then dipped for 5 seconds into aqueous formulations of the active ingredients and excess liquid was allowed to drip off onto filter paper, care being taken to prevent the eggs coming into contact with the paper.

The markers were than placed in plastic trays (adhesive strip at the top). Half a roll of absorbent cotton was moistened with water and placed in each beaker to prevent drying out, and the trays were covered with a glass plate. Assessment took place after the control bugs hatched (after about 8 days).

In this experiment, the lethal dose of compounds 33, 39, 41, 61 and 63 was either 0.1 wt% or less. Compounds 36, 37 and 58 achieved a kill rate of 80% at a dosage of 0.04 wt% or less.

We claim:

1. A 3,4-Dihydro-2H-pyran of the formula

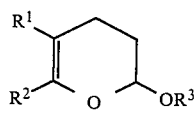
(I)

where $R^1$ is $C_4$–$C_{20}$-alkyl, $C_4$–$C_{20}$-alkoxyalkyl, phenyl or $C_7$–$C_{20}$-phenylalkyl, or is phenyl or $C_7$–$C_{20}$-phenylalkyl which bears from one to three substituents selected from the group consisting of halogen, $C_1$–$C_8$-alkyl, $C_1$–$C_8$-haloalkyl, $C_1$–$C_8$-alkoxy or $C_1$–$C_8$-haloalkoxy, $R^2$ is hydrogen or $C_1$–$C_4$-alkyl, $R^3$ is the radical

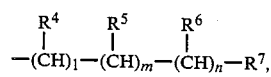

where $R^4$, $R^5$ and $R^6$ are hydrogen or $C_1$–$C_4$-alkyl, $R^7$ is phenyl or benzoyl, or phenyl or benzoyl bearing from one to three substituents selected from the group consisting of halogen, $C_1$–$C_8$-alkyl, $C_8$-alkyl, $C_1$–$C_8$-haloalkyl, $C_1$–$C_8$-alkoxy and $C_1$–$C_8$-haloalkoxy, or a five- or six-membered heterocycle containing one or two oxygen atoms and which is either unsubstituted or substituted by one to three $C_1$–$C_8$-alkyl groups or one $C_3$–$C_6$-spirocycloalkyl, and l, m and n are 0 or 1.

2. 3,4-Dihydro-2H-pyran as set forth in claim 1, where $R^1$ is $C_4$–$C_{20}$-alkyl, $C_4$–$C_{20}$-alkoxyalkyl or $C_7$–$C_{20}$-phenylalkyl, $R^2$ is hydrogen or $C_1$–$C_4$-alkyl, and $R^3$ is fluoro- or chloro-substituted phenyl.

3. 3,4,-Dihydro-2H-pyran as set forth in claim 1, where $R^1$ is $C_4$–$C_{20}$-alkyl, $C_4$–$C_{20}$-alkoxyalkyl or $C_7$–$C_{20}$-phenylalkyl, $R^2$ is hydrogen or $C_1$–$C_4$-alkyl, and $R^3$ is the radical $$-(CH_2)_1\text{-}(CH_2)_m\text{-}R^7$$

where $R^7$ is a substituted or unsubstituted dioxane or dioxolane radical, and l and m are 0 or 1.

4. A pesticide containing a 3,4-dihydro-2H-pyran of the formula I as set forth in claim 1, and conventional additives.

5. A pesticide as set forth in claim 4, containing from 0.1 to 95wt % of a 3,4-dihydro-2H-pyran.

6. A process for combating pests, wherein the pests or the areas or spaces to be kept free from pests, are treated with a pesticidally effective amount of a 3,4-dihydro-2H-pyran of the formula I as set forth in claim 1.

* * * * *

UNITED STATES PATENT AND TRADEMARK OFFICE
CERTIFICATE OF CORRECTION

PATENT NO. : 4,876,275

DATED : October 24, 1989

INVENTOR(S) : Walter HIMMELE et al.

It is certified that error appears in the above-identified patent and that said Letters Patent is hereby corrected as shown below:

Claim 1, column 16, line 4 that part of line 4 reading "$C_1$-$C_8$-alkyl, $C_8$-alkyl, $C_1$-$C_8$-haloal-" should read --$C_1$-$C_8$-alkyl, $C_1$-$C_8$-haloal- --

Signed and Sealed this

Ninth Day of July, 1991

Attest:

HARRY F. MANBECK, JR.

*Attesting Officer*

*Commissioner of Patents and Trademarks*